US009999632B2

(12) United States Patent
Richardson et al.

(10) Patent No.: US 9,999,632 B2
(45) Date of Patent: *Jun. 19, 2018

(54) INHIBITION OF PANCREATIC LIPASE

(71) Applicants: RD Biomed Limited, Hull (GB); University of Newcastle upon Tyne, Tyne and Wear (GB)

(72) Inventors: Johnathan Craig Richardson, Notts (GB); Peter William Dettmar, East Yorkshire (GB); Matthew David Wilcox, Tyne and Wear (GB); Iain Andrew Brownlee, Sheffield (GB); Jeffrey Peter Pearson, County Durham (GB)

(73) Assignees: RD Biomed Limited (GB); University of Newcastle upon Tyne (GB)

( * ) Notice: Subject to any disclaimer, the term of this patent is extended or adjusted under 35 U.S.C. 154(b) by 21 days.

This patent is subject to a terminal disclaimer.

(21) Appl. No.: 15/221,144

(22) Filed: Jul. 27, 2016

(65) Prior Publication Data

US 2017/0014447 A1  Jan. 19, 2017

Related U.S. Application Data

(63) Continuation of application No. 13/512,118, filed as application No. PCT/GB2010/002181 on Nov. 25, 2010, now Pat. No. 9,402,858.

(30) Foreign Application Priority Data

Nov. 25, 2009  (GB) .................................. 0920633.5

(51) Int. Cl.
*A61K 31/734* (2006.01)

(52) U.S. Cl.
CPC .................................. *A61K 31/734* (2013.01)

(58) Field of Classification Search
CPC .................................................. A61K 31/734
See application file for complete search history.

(56) References Cited

U.S. PATENT DOCUMENTS

| | | | |
|---|---|---|---|
| 5,017,565 A | 5/1991 | Lange, III et al. |
| 5,063,210 A | 11/1991 | Lange, III et al. |
| 5,234,526 A | 8/1993 | Chen et al. |
| 5,484,777 A | 1/1996 | Lange, III et al. |
| 5,616,570 A | 4/1997 | Lange, III et al. |
| 6,432,400 B1 | 8/2002 | Chapus |
| 6,497,910 B2 | 12/2002 | Takahashi et al. |
| 6,899,892 B2 | 5/2005 | Gallaher et al. |
| 2002/0001659 A1 | 1/2002 | Takahashi et al. |
| 2003/0176394 A1 | 9/2003 | Dettmar et al. |
| 2004/0038909 A1 | 2/2004 | Chawan |
| 2005/0170059 A1 | 8/2005 | Aldred et al. |
| 2006/0228397 A1 | 10/2006 | Gahler et al. |
| 2007/0082026 A1 | 4/2007 | Aimutis et al. |
| 2007/0082084 A1 | 4/2007 | Catani et al. |
| 2007/0082107 A1 | 4/2007 | Aimutis et al. |
| 2007/0082108 A1 | 4/2007 | Aimutis et al. |
| 2007/0082115 A1 | 4/2007 | Aimutis et al. |
| 2008/0027024 A1 | 1/2008 | Gahler et al. |
| 2009/0068281 A1 | 3/2009 | Toyomura et al. |
| 2011/0098245 A1 | 4/2011 | Suzuki et al. |

FOREIGN PATENT DOCUMENTS

| | | |
|---|---|---|
| CN | 1097307 A | 1/1995 |
| EP | 0469079 A1 | 2/1992 |
| EP | 0493265 A1 | 7/1992 |
| EP | 1010370 A2 | 6/2000 |
| EP | 1064858 A2 | 1/2001 |
| EP | 2074891 A1 | 7/2009 |
| JP | H03290170 | 12/1991 |
| JP | 5186356 A | 7/1993 |
| JP | H07147935 A | 6/1995 |
| JP | 2000236821 A | 9/2000 |
| JP | 2007330124 | 12/2007 |
| WO | WO-03053469 A1 | 7/2003 |
| WO | WO-2005020717 A1 | 3/2005 |
| WO | WO-2005036971 A1 | 4/2005 |
| WO | WO-2006108283 A1 | 10/2006 |
| WO | WO-2007070135 A1 | 6/2007 |
| WO | WO-2007148197 A2 | 12/2007 |
| WO | WO-2008098579 A1 | 8/2008 |
| WO | WO-2011063809 A1 | 6/2011 |
| WO | WO-2011063817 A2 | 6/2011 |
| WO | WO-2011064547 A1 | 6/2011 |
| WO | WO-2012044242 A1 | 4/2012 |

OTHER PUBLICATIONS

William C. Vogel et al., "A Rapid and sensitive Turbidimetric Method for Serum Lipase Based Upon Differences Between the Lipases of Normal and Pancreatitis Serum", Radioisotope Service and Department of Medicine, Veterans Administration Hospital, University of Minnesota, Minneapolis 17, Minn., vol. 9, No. 2, 1963, pp. 168-181.
Documenta Geigy, Scientific Tables, Sixth Edition, 1962, Edited by Konrad Diem, Published by Geigy Pharmaceutical Company Limited, Manchester, pp. 517-525.
Stern et al., "Inhibition of Lipolytic Activity in Milk by Polysaccharides", J. Dairy Sci, 1988, 71 (1), p. 41-45.
Sharma, Shweta, et al., "Alginate as a macroaffinity ligand and an additive for enhanced activity and thermostability of lipases", Biotechnology and Applied Biochemistry; Jun. 2001, 5 pages.
Birari, Rahul, et al., "Pancreatic lipase inhibitors from natural sources: unexplored potential", Drug Discovery Today, vol. 12, No. 19/20, Oct. 11, 2007, 11 pages.
Paxman, J.R., et al., "Daily ingestion of alginate reduces energy intake in free-living subjects", Appetite, Academic Press, New York, Nov. 1, 2008, 7 pages.
Ozyilmaz, Gul, et al., "Production of aroma esters by immobilized Candida rugosa and porcine pancreatic lipase into calcium alginate gel", Journal of Molecular Catalysis B: Enzymatic, Jul. 1, 2010, 6 pages.
Li, Yan, et al., "Control of Lipase digestibility of emulsified lipids by encapsulation within calcium alginate beads", Food Hydrocolloids, Elsevier, Jan. 1, 2011, 9 pages.
Alginates, FMC BioPolymer bulletin, 2003, FMC Corporation, p. 1-14.
Ikeda et at., "In Vitro Inhibition of Digestive Enzymes by Indigestible Polysaccharides", Cereal Chemistry, 1983, 60(4), p. 260-263.
Spiller, G.A., ed., CRC Handbook of dietary fiber in human nutrition, 2001, CRC Press LLC, p. 277-285.

(Continued)

*Primary Examiner* — Jonathan S Lau
(74) *Attorney, Agent, or Firm* — Fox Rothschild LLP

(57) ABSTRACT

The present invention provides the use of an alginate Io inhibit pancreatic lipase. The use may be directed to the control of weight in animals including human beings. Preferably the fraction of guluronate dimers in the alginate is at least 0.5.

11 Claims, 13 Drawing Sheets

(56) References Cited

OTHER PUBLICATIONS

Ann-Sofie Sandberg et al., "Alginate, small bowel sterol excretion, and absorption of nutrients in ileostomy subjects", American Journal of Clinical Nutrition, Nov. 1994, vol. 60 No. 5, 751-756.

Stokke et al., "Distribution of Uronate Residues in Alginate Chains in Relation to Alginate Gelling Properties", Macromolecules, 1991, 24, pp. 4637-4645.

Gomez et al., Influence of the extraction-purification conditions on final properties of alginates obtained from brown algae (Macrocystis pyrifera), International Journal of Biological Macromolecules, 2009, 44, pp. 365-371.

Written Opinion & International Search Report for PCT/GB2010/002181 dated Apr. 8, 2011, 15 pages.

INHIBITION OF PANCREATIC LIPASE

CROSS-REFERENCES TO RELATED APPLICATIONS

This application is a continuation of and claims priority to U.S. patent application Ser. No. 13/512,118, filed Aug. 2, 2012, which is a U.S. national stage under 35 U.S.C. § 371 of International Patent Application No. PCT/GB2010/002181, filed Nov. 25, 2010, which claims priority to GB Patent Application No. 0920633.5, filed Nov. 25, 2009.

THE FIELD OF THE INVENTION

This invention relates to the inhibition of pancreatic lipase and includes compounds, compositions and processes for so doing.

BACKGROUND TO THE INVENTION

Alginate is an unbranched polysaccharide containing two epimers of uronic acid [1]. Mannuronic acid (M) and its C-5-epimer guluronic acid (G) are linked by α and β (1→4) glycosidic bonds [2]. The composition of an alginate can be calculated by nearest neighbour diad frequency using $^{13}C$ nuclear magnetic resonance (NMR) spectroscopy [3]. Brown seaweed is a major commercial source of alginate, where it occurs as a structural component of the cell wall. The arrangements of the acid residues are of great importance as they confer specific characteristics. Higher levels of M residues give an increase in flexibility of that section of seaweed. For example, the highest level of M residues of *Laminaria hyperboria* is found in the leaf tissue whereas the stipe is much lower in M residues, with the outer cortex even lower [4]. Alginates are not only exploited by algae, but also by bacteria. In the soil bacteria, *Azotobacter vinlandii*, alginates are the major constituents of the vegetative capsule and of the rigid and desiccation-resistant walls of the metabolically dormant cysts [5]. The alginates produced by many bacteria, for example *Pseudomonas* spp. appear to have multiple roles in environmental protection whereas both bacterial and seaweed alginates can stimulate the human immune system [5].

Enzymes that possess the ability to epimerise M residues to G residues have been isolated and purified from bacterial strains that utilise alginates. A family of seven epimerase enzymes (AlgE1-7) have been purified from *A. vinlandii* and their activity described. Each enzyme is likely to produce a distinct monomer distributions pattern, for example AlgE1 is the only double epimerasic enzyme creating two consecutive G residues whereas the other epimerase enzymes can only affect one residue at a time. Bacterial alginates can be created as homopolymeric M residue polymers and can then be processed by the enzymes to their desired characteristics. Epimerase negative stains of *Pseudomonas fluorescens* have been developed which allows alginates of purely M residues to be harvested when the bacteria are grown on media containing a high concentration of D-fructose-6-phosphate [6].

A varying range of lipases are produced within the human body as well as by bacteria, all of which are responsible for the catalysis of hydrolysis of ester bonds in triacylglycerols. With the exception of pancreatic lipase, all lipases are single domain enzymes. Pancreatic lipase requires another protein (colipase) for activity in the presence of bile salts or detergents [7]. Colipase (11000 Da) is involved with the activity of the enzyme, prevention of denaturation at the water-lipid interface and reverses the inhibitory effect of bile salts at the same interface. There are two conformations of pancreatic lipase, the open (active) form and the closed (inactive) form [8]. The conformation is changed via the movement of two loops of amino acids uncovering the hydrophobic active site. The binding of the colipase does not initiate activity of the enzyme nor does it initiate the movement of the loops but, when the colipase is bound at the lipid-water interface, the loops make multiple contacts with the colipase when in the open conformation [8]. There is a common fold throughout all the lipases termed the α/β hydrolase fold due to the orientation of the α-helices and the arrangement of the β-strands. The active site of the pancreatic lipase is composed of a catalytic serine-histadine-aspartate triad and this triad is well conserved throughout the lipase family [8]. The lipid substrate is likely to enter the active site in a 'tuning fork' orientation [9] with one acyl chain (one prong) in the active site and the second acyl chain (second prong) running along the outside of the lipase molecule in a groove created by two phenylalanine residues [10].

Some pharmacological obesity treatments, e.g. Orlistat (Trade Mark), function through specific, irreversible inhibition of gastrointestinal lipases, of which pancreatic lipase is the most biologically active and important in healthy humans [11]. A number of adverse effects are commonly reported for Orlistat, including steatorrhoea, bloating, oily spotting, faecal urgency and faecal incontinence that can affect up to 40% of patients [12]. This leads to high attrition rates and tolerability problems. A product which retains the level of lipase inhibition but reduces or eliminates the adverse effects of current treatment would be of considerable benefit to patients.

STATEMENTS OF THE INVENTION

According to the present invention there is provided a use of an alginate to inhibit pancreatic lipase. The alginate may be derived from any suitable source, including seaweed. It may be a bacterial alginate, in particular, an alginate that has not been epimerised (i.e. alginate 1:PAG) It may alternatively be a synthetic alginate.

Preferably the fraction of the guluronate residues in the alginate is at least 0.5.

Preferably the fraction of the guluronate dimers in the alginate is at least 0.3.

Preferably the fraction of guluronate trimers in the alginate is at least 0.25.

Preferably the fraction of MGM blocks in the alginate is less than 0.2.

The inhibition of pancreatic lipase may be directed, wholly or partly, to the control of weight in animals, including human beings.

The present invention also provides a method of inhibiting pancreatic lipase in an animal, including a human being, comprising administration of an effective amount of an alginate.

Preferably the amount of alginate administered is from 0.1 to 10 g as a daily dosage, more preferably 0.5 to 10 g as a daily dosage and most preferably 0.5 g to 8 g as a daily dosage The present invention also provides a weight control composition comprising an alginate in admixture with one or more adjuvants, diluents or carriers which are acceptable for consumption by animals, including human beings.

DETAILED DESCRIPTION OF THE INVENTION

Figure 1:
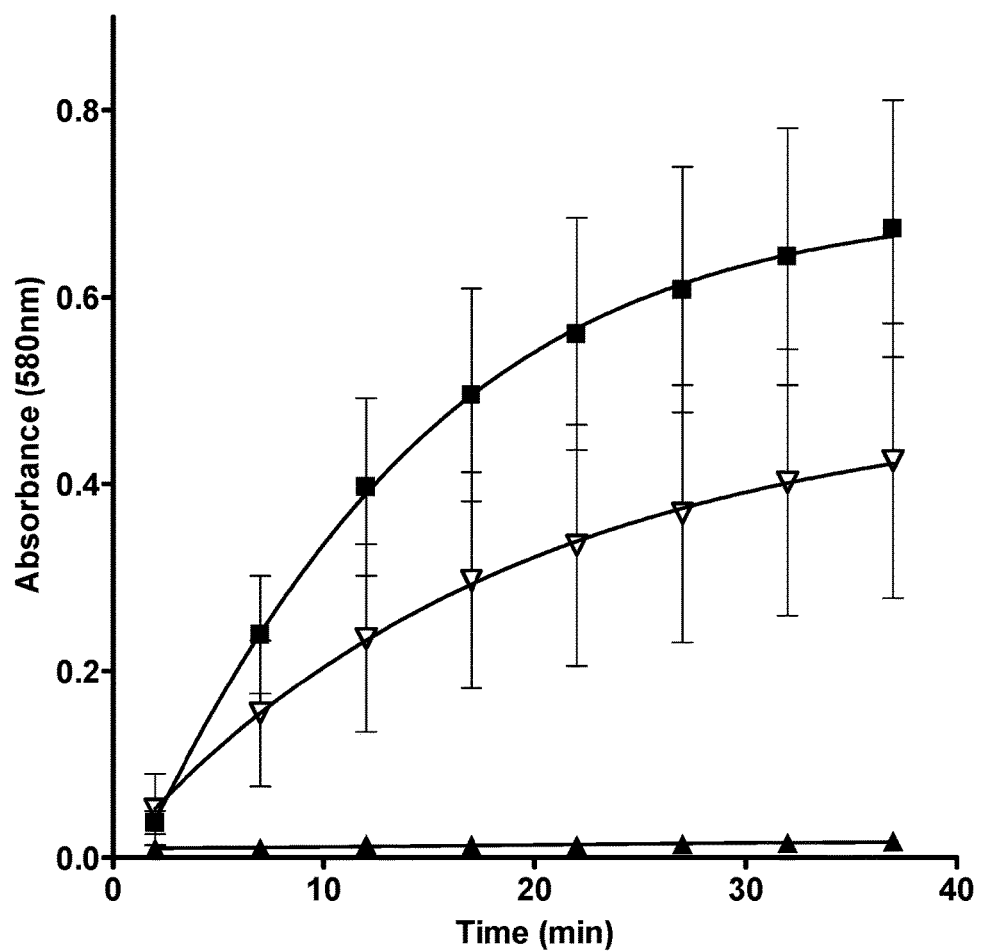
FIG. 1 is a graph showing the absorbance change over time as a measure of lipase activity. Filled squares—Lipase control (lipase plus substrate), open inverted triangles —alginate SF200 at 3.43 mg/ml (as an example) and filled triangles—Inhibition control 0.025 mg/ml Orlistat. The error bars show the standard error of the mean (n=6).

The invention will now be described, by way of examples only:

EXAMPLE 1

Experimental Section
Materials

All alginate samples were kindly provided by Technostics (Hull, UK and FMC BioPolymer, Norway). The tris(hydroxymethyl)-methylamine and calcium chloride were purchased from BDH (Poole, UK). Bile acids (deoxycholic acid sodium salt and taurodeoxycholic acid sodium salt) were both purchased from Fluka (Buchs, Switzerland), whereas the 1,2 Di-o-lauryl-rac-glycero-3-(glutaric acid 6-methyl resorufin ester) (DGGR), sodium acetate, colipase, lipase and Orlistat (tetrahydrolipstatin) were all purchased from Sigma-Aldrich (Poole, UK).

Equipment

Absorbance was measured at 580 nm using an ATI Unicam 8625 UV/VIS spectrophotometer with semi-micro cuvettes (10 mm light path) (Fisher, UK FB55147) or a 96 well microplate spectrophotometer using a 575 nm filter (EL808 BioTek, Bedfordshire UK)

Preparation

The lipase activity assay is a modified version of the method developed by Panteghini et al. [13]. The assay requires three solutions, Solution 1, Solution 2 and the Lipase solution. Solution 1 contains 1 mg/l of colipase and 1.8 mmol/l deoxycholic acid sodium salt in Tris buffer (50 mmol/l pH 8.4 at 25° C.). Solution 2 contains 72 mmol/l taurodeoxycholic acid sodium salt, 0.1 mmol/l calcium chloride and 0.24 mmol/l DGGR in acetate buffer (18 mmol/l, pH 4.0 at 25° C.). Solution 2 was mixed on a magnetic stirrer at 500 rpm and 4° C. overnight. The lipase solution contains 1 g/l of porcine pancreatic lipase in deionised water, where 1 mg contains 60 U of lipase activity.

For all alginate polymer samples, a stock solution containing 4 g/l polymer was prepared by slowly adding dry polymer powder to a vortexing mixture of Solution 1. The stock solution was then diluted with buffer to produce polymer test samples containing 0.25, 1 and 4 g/l polymer. When the three polymer test samples were added to the reaction mixture, the alginate concentration in the reaction mixture was 0.21, 0.86 and 3.43 g/l respectively. As a positive control, 0.025 g/l Orlistat was added to Solution 1. All solutions were stored at 4° C. until use.

Procedure

Lipase Activity Assay

The activity of lipase was assessed under three conditions. Firstly, lipase activity was determined under optimum assay conditions where 100% activity is achievable. These conditions are referred to as Lipase Control conditions.

1.5 ml of Solution 1 was mixed with 100 µl of Lipase Solution and incubated at 37° C. for 60 minutes. In tandem, 150 µl of Solution 2 was also incubated at 37° C. for 60 minutes before being combined with the Solution 1: Lipase Solution mixture and then incubated for a further 35 minutes. Once Solution 2 had been added to the enzyme mixture a two minute lag phase was observed and then the absorbance was read at five minute intervals for 35 minutes at either 575 nm for the plate assay or 580 nm for the cuvette assay. Reagent blanks were also run to eliminate the effect that additional chemicals have on the absorbance. To achieve this 100 µl of deionised water replaced the 100 µl of lipase solution added to the test condition. The respective reagent blanks were subtracted from their control or test condition.

The second condition under which lipase activity was assessed was in the presence of a known covalent inhibitor, tetrahydrolipstatin (Orlistat). Under these conditions 0.025 g/l of Orlistat was added to Solution 1 prior to incubation and the assay methodology above was followed. Orlistat completely inhibits lipase and was used as a positive control for inhibition. These conditions are referred to as Inhibition Control conditions The final condition in which lipase activity was assessed was in the presence of alginate polymer. Polymers were added to Solution 1 (0.25-4 g/l) prior to incubation and the assay methodology above followed. These conditions are referred to as Test Condition.

To calculate the percentage of lipase inhibition by alginates, the absorbance values under Test Conditions, Inhibition Control conditions and Lipase Control conditions were used and the following formula applied.

Percentage of Lipase inhibition=
$$1 - \frac{\text{Test Condition} - \text{Inhibition Control}}{\text{Lipase Control} - \text{Inhibition Control}} \times 100$$

The absorbance values used for the enzyme inhibition calculation were measurements taken after Solutions 1, 2 and lipase solution has been incubated for 12 minutes. At this stage the reaction was still in its linear phase.

All lipase activity assays were repeated six times.

Lipase will cleave the DGGR substrate to form 1,2 Di-o-lauryl-rac-glycerol and glutaric acid a 6-methyl resorufin ester compound. The ester will then spontaneously hydrolyses under alkaline conditions to glutaric acid and produce a purple chromophore (methyl resorufin). The increase in absorbance at 575-580 nm is a measure of lipase activity. The Cuvette assay was adapeted for a 96 well microplate assay. The procedure and method remained the same, however a tenfold reduction in volume was applied to allow the volumes to fit on a plate.

Statistical Analysis

All statistical analysis and graph drawing were performed using standard functions of the analysis software Prism version 4 (GraphPad, San Diego, USA).

EXAMPLE 2

Alginate XP3663
Method

The lipase activity assay is a modified version of the method developed by Panteghini et al. [13]. The assay is comprised of three solutions, solution 1, solution 2 and the lipase solution. Solution 1 contains per liter of Tris buffer (50 mmol/l pH 8.4 at 23° C.), 1 mg of colipase and 1.8 mmol deoxycholic acid sodium salt. Solution 2 contains per liter of acetate buffer (18 mmol/1, pH 4.0 at 23° C.) 72 mmol taurodeoxycholic acid sodium salt, 0.1 mmol calcium chloride, and 0.24 mmol DGGR. Solution 2 was mixed with a magnetic stirrer at 500 rpm and 4° C. overnight. The lipase solution contains 1 g/l of porcine pancreatic lipase in deionised water, where 1 mg contains 60 U of lipase activity.

Alginate polymer (either XP3663 or LFR5/60) was added slowly to a vortexing solution 1, achieving a concentration of 4 g/l which was in turn diluted to 1 g/l and 0.25 g/l. This achieved a concentration of 3.43 g/l, 0.86 g/l and 0.21 g/l respectively in the reaction mixture. To achieve 100% inhibition in the assay system 0.025 g/l Orlistat was added to solution 1. All solutions were stored at 4° C. until use.

12 µl of lipase solution was added to either 180 µl solution 1, 180 µl the test polymer in solution 1 or 180 µl orlistat in solution 1. The test polymer in solution 1 (either XP3663 and LFR5/60) was present at the following concentrations (4, 1, or 0.25 g/l). Once incubated for one hour at 37° C., 160 µl of the above solutions were added to the substrate solution (15 µl of solution 2), thereby initiating the reaction. As a blank, the above procedure was repeated using 12 µl of deionised water instead of 12 µl of lipase solution. The absorbance of the reaction was measured at 575 nm every five minutes for 35 minutes after an initial two minute lag phase. To calculate the percentage of lipase inhibition, the reagent blanks were subtracted from the corresponding controls or samples and the following equation was applied:

Percentage of Lipase inhibition=
$$1 - \frac{\text{Polymer Sample} - \text{Inhibition Control}}{\text{Lipase Control} - \text{Inhibition Control}} \times 100$$

As an example, if biopolymer x achieved an absorbance measurement of 0.6 absorbance units, with its respective blank containing the biopolymer and no enzyme achieved 0.19 absorbance units, then the overall value used in the above equation would be 0.41 absorbance units. If the inhibition control achieved a reading of 0.3 absorbance units, with its blank achieving 0.25 absorbance units, then the value used in the equation above would be 0.05 absorbance units. The value that would be used for the lipase control would be 0.85 absorbance units after the blank of 0.12 had been subtracted if the reaction achieves an absorbance reading of 0.97 absorbance units. Therefore the equation would read;

$$\text{Percentage of Lipase inhibition} = 1 - \frac{0.41 - 0.05}{0.85 - 0.05}$$

Therefore biopolymer x would have inhibited pancreatic lipase by 55%

There were two biopolymers tested in this assay system, alginates XP3663 and LFR5/60. The two alginates were tested at the same time on the same plate using the same solutions. The two alginates were tested six times using fresh solutions each time.

Results

FIG. 1 illustrates how the activity of lipase (shown as an increase in absorbance over time) varied under the three conditions described above. Under the Lipase Control conditions (100% lipase activity) absorbance increased linearly up to 12 minutes before plateauing to a maximal value. FIG. 1 also shows that Orlistat (0.025 mg/ml), an effective inhibitor of lipase provided a positive control for inhibition in the assay. The Orlistat positive control showed no inhibition and yielded the maximum rate of the reaction (FIG. 1: Inhibition control). Finally, FIG. 1 highlights how a polymer (alginate SF200) can inhibit lipase, as shown by a reduction in the level of absorbance with time compared to the Lipase Control conditions.

Figure 2:
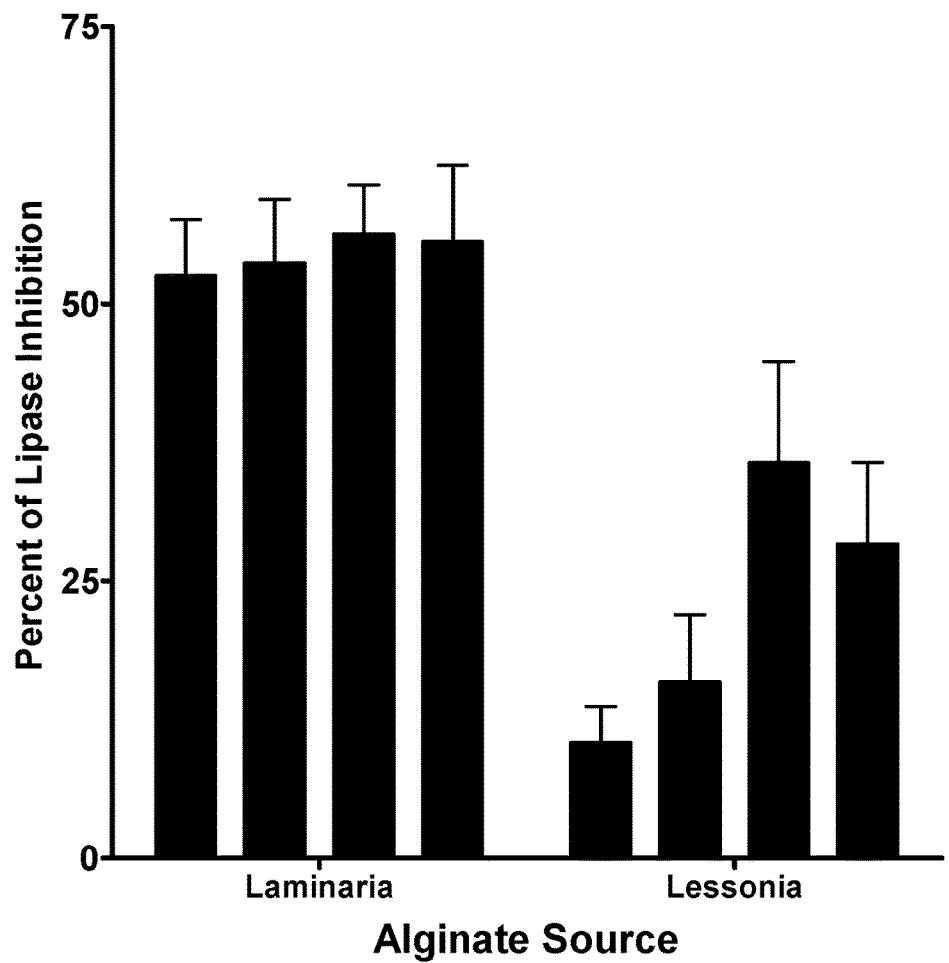
FIG. 2 is a bar chart showing a comparison between alginates from *Laminaria* and *Lessonia* seaweed. Four alginates of increasing molecular weight (from left to right) are shown for *Laminaria* and *Lessonia* as their respective source. Inhibition of lipase shown in this figure is caused by 3.43 mg/ml of alginate. The alginates from *Laminaria* species are LFR5/60, SF120, SF/LF, and the *Lessonia* seaweed alginates are LF10L, LF120L, SF60 and H120L. Error bars shown are the standard error of the mean (n=6).

FIG. 2, shows the percentage lipase inhibition achieved by eight brown seaweed alginates (four extracted from *Laminaria* and four extracted from *Lessonia*). All the alginates reduced the activity of lipase; however, there was a significant difference in the level of inhibition dependent on the seaweed source of alginate. The alginates extracted from *Laminaria* seaweed inhibited pancreatic lipase to a significantly higher degree (p>0.001) than the alginates extracted from *Lessonia*.

Figure 3:
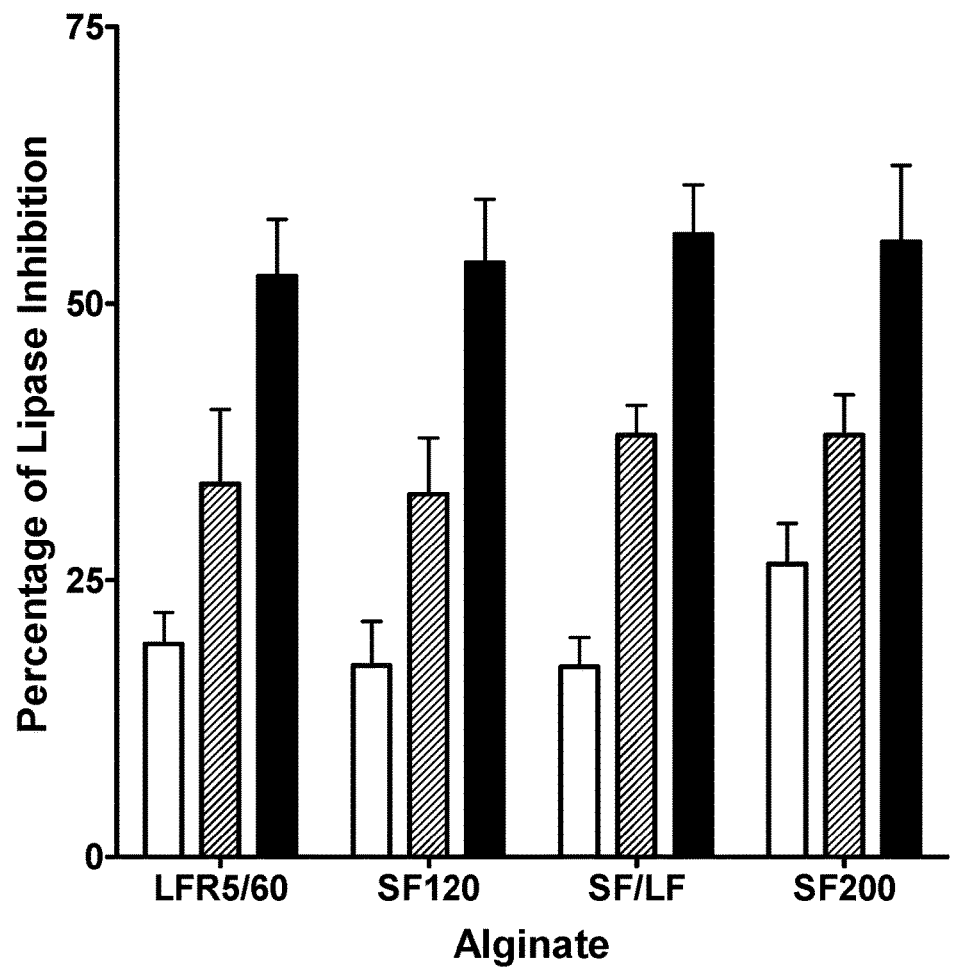
FIG. 3 is a bar chart illustrating the concentration dependent inhibition of lipase by the four alginates from *Laminaria* genus of seaweeds. Open bars—0.21 mg/ml, hatched bars—0.86 mg/ml, and solid filled bars—3.43 mg/ml. The error bars are the standard error of the mean (n=6).

FIG. 3 illustrates that the inhibition of lipase by alginates was concentration dependent. Although FIG. 3 only shows alginates from *Laminaria*, for all alginates tested increasing the dose of alginate achieved a higher level of pancreatic lipase inhibition.

FIGS. 2 and 3 both show that not all alginates inhibit lipase to the same extent, even those from the same genus. A possible explanation is there are variations in the chemical composition of alginates. More specifically, there are distinct differences in the content and arrangement of constituent guluronic and mannuronic acid blocks.

The structural characteristics of alginates tested in this study are listed in Table 1. Polymer 1 as listed in the table is a homopolymeric mannuronate alginate from a bacterial source, polymers 2-15 are from either a bacterial or seaweed source and have had their initial structure altered using one or a combination of epimerase enzymes. For example the bacterial alginate PAB has been enzymatically altered from a homopolymeric M block alginate (PAG) via incubation with an alternating epimerase enzyme until completion, creating a polymer of mainly alternating MG blocks. The alginate PAT was only treated with the same epimerase enzyme for 2 hours, therefore only increasing the MG content from 0 to 17%. Polymers 16-19 are from the *Laminaria* seaweed source whereas the final polymers listed (20-23) are from *Lessonia* seaweed sources.

in an alginate and its ability to inhibit lipase. This indicates that increasing the fraction of guluronate increases the level of lipase inhibition (p=0.01). Conversely increasing the fraction of mannuronate in an alginate (FIG. 5) decreases the level of lipase inhibition (r=−0.506 and p=0.01). This would be expected, because increasing the content of one uronic acid unit automatically decreases the fraction of the other.

Figure 6:
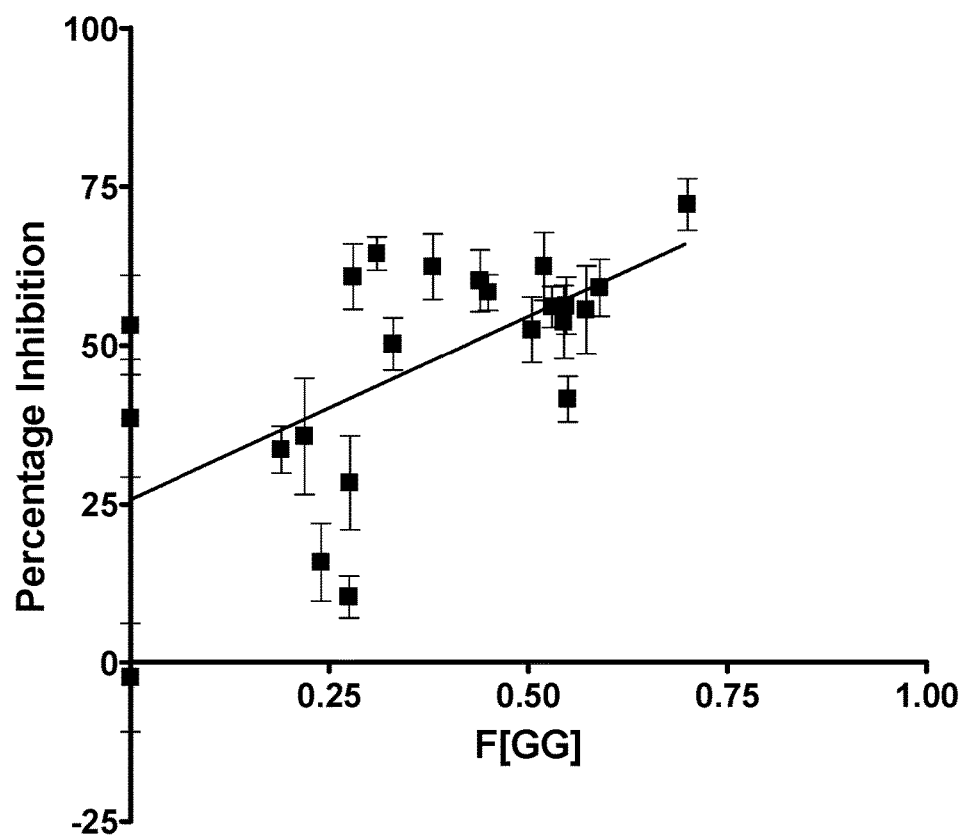
FIG. 6 is a graph showing the percentage of lipase inhibition at 12 minutes using 3.43 mg/ml alginate against the fraction of guluronate dimmers (F[GG]) in the alginate polymers. Error bars shown are the standard error of the mean (n=6).
Figure 7:
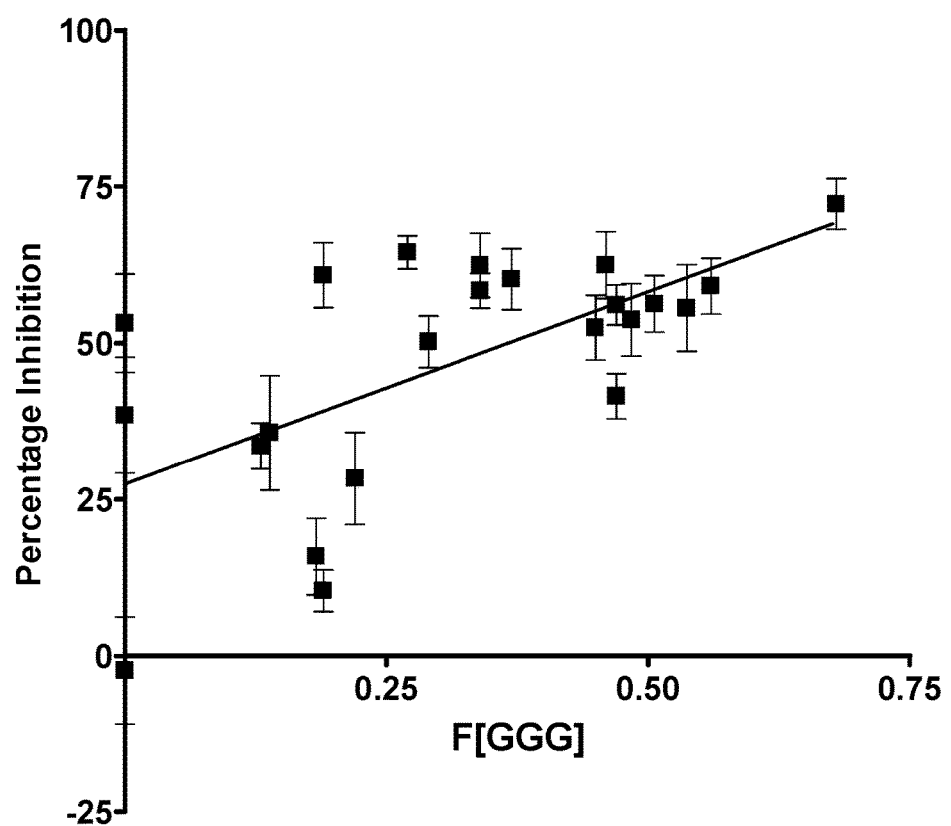
FIG. 7 is a graph showing the percentage of lipase inhibition at 12 minutes using 3.43 mg/ml alginate plotted against the fraction of guluronate trimers (F[GGG]) in the alginate polymers. Error bars show the standard error of the mean (n=6).

FIGS. 6 and 7 show that similar significant relationships are observed when comparing the fraction of guluronic acid dimers (F(GG)) or trimers (F(GGG)) with the level of inhibition. Increasing the fraction of GG blocks (FIG. 6) and increasing the fraction of GGG blocks (FIG. 7) in an alginate increases the inhibition of lipase. The correlations in FIGS. 6 and 7 are positive and significant, confirmed with Spearman r values of 0.583 and 0.578 and p values of 0.004

Figure 8:
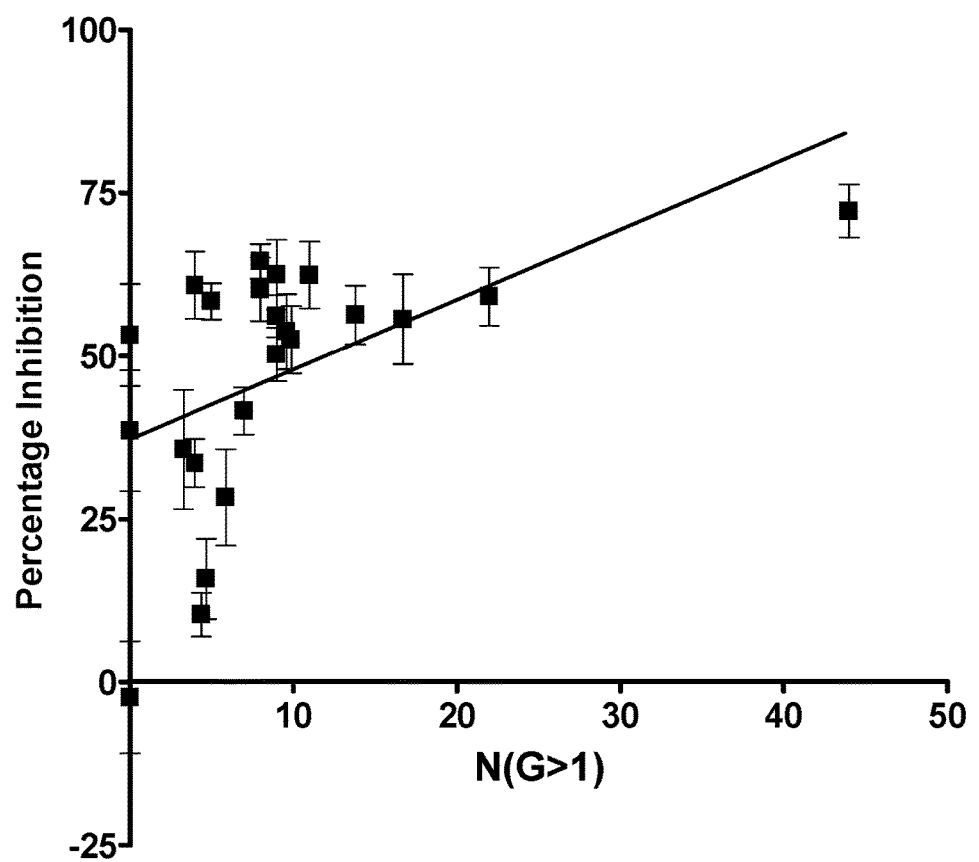
FIG. 8 is a graph showing the percentage of lipase inhibition at 12 minutes using 3.43 mg/ml alginate against the average length of guluronate blocks (N(G>1)) in the alginate polymers. Error bars show the standard error of the mean (n=6).

Furthermore, FIG. 8 identifies a correlation between the size of the guluronic acid block length (N(G>1)) and the ability of the alginate to inhibit lipase. It is clear that the larger the guluronic acid block length the greater the ability of alginate to inhibit lipase. The Spearman r value is 0.586 and the p value for the correlation is 0.003.

Figure 9:
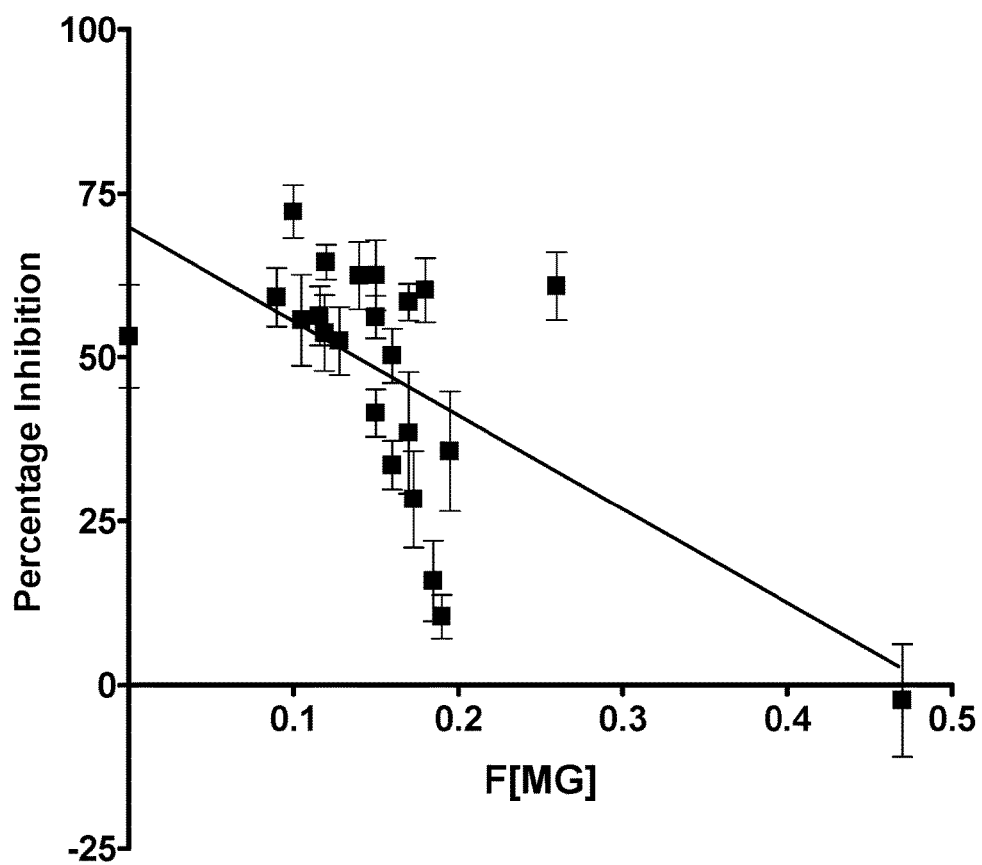
FIG. 9 is a graph showing the percentage of lipase inhibition at 12 minutes using 3.43 mg/ml alginate plotted against the fraction of either MG or GM blocks (F[MG]) in the alginate polymers. Error bars shown are the standard error of the mean (n=6).

FIG. 9 shows a further relationship between alginate composition and lipase inhibition. There appears to be an inverse relationship between the fraction of MG or GM blocks in alginate and lipase inhibition. The correlation in FIG. 9 is negative and has a Spearman r value of −0.505 and a p value of 0.01. It would appear the correlation may be distorted by the value showing negative inhibition with a F(MG) of 0.47. This value was generated from the unique bacterial alginate that is an almost entirely alternating M and G residue polymer after treatment with an epimerase enzyme. However, when this point is removed from the

TABLE 1

Sources, code and characteristics of the alginates used in the study

| | Alginate Source | Sample Code | Molecular Wt | F(G) | F(M) | F(GG) | F(GM) = F(MG) | F(MM) | F(MGG) = F(GGM) | F(MGM) | F(GGG) | N(G > 1) |
|---|---|---|---|---|---|---|---|---|---|---|---|---|
| 1 | Bacterial | PAG | 584400 | 0 | 1 | 0 | 0 | 1 | 0 | 0 | 0 | 0 |
| 2 | Bacterial (treated with epimerase) | PAB | 456733 | 0.47 | 0.53 | 0 | 0.47 | 0.059 | 0 | 0.47 | 0 | 0 |
| 3 | Bacterial (treated with epimerase) | PAE | 436767 | 0.52 | 0.48 | 0.38 | 0.14 | 0.34 | 0.037 | 0.12 | 0.34 | 11 |
| 4 | Bacterial (treated with epimerase) | PAF | 442367 | 0.44 | 0.56 | 0.31 | 0.12 | 0.44 | 0.04 | 0.1 | 0.27 | 8 |
| 5 | Bacterial (treated with epimerase) | PAA | 423767 | 0.8 | 0.2 | 0.7 | 0.1 | 0.1 | 0.016 | 0.094 | 0.68 | 44 |
| 6 | Bacterial (treated with epimerase) | PAD | 194833 | 0.54 | 0.46 | 0.28 | 0.26 | 0.2 | 0.084 | 0.21 | 0.19 | 4 |
| 7 | Seaweed (treated with epimerase) | PAC | 262400 | 0.7 | 0.3 | 0.55 | 0.15 | 0.15 | 0.083 | 0.086 | 0.47 | 7 |
| 8 | Bacterial (treated with epimerase) | PAI | 374800 | 0.68 | 0.32 | 0.59 | 0.09 | 0.23 | 0.028 | 0.077 | 0.56 | 22 |
| 9 | Seaweed (treated with epimerase) | PAJ | 211833 | 0.62 | 0.38 | 0.44 | 0.18 | 0.2 | 0.067 | 0.115 | 0.37 | 8 |
| 10 | Seaweed (treated with epimerase) | PAK | 202000 | 0.62 | 0.38 | 0.45 | 0.17 | 0.21 | 0.115 | 0.091 | 0.34 | 5 |
| 11 | Seaweed *Durvillea potatorum* | PAL | 241067 | 0.35 | 0.65 | 0.19 | 0.16 | 0.49 | 0.05 | 0.13 | 0.13 | 4 |
| 12 | Seaweed (treated with epimerase) | PAM | 251220 | 0.68 | 0.32 | 0.53 | 0.15 | 0.16 | 0.064 | 0.118 | 0.47 | 9 |
| 13 | Seaweed (treated with epimerase) | PAN | 226550 | 0.67 | 0.33 | 0.52 | 0.15 | 0.18 | 0.063 | 0.081 | 0.46 | 9 |
| 14 | Seaweed *Laminaria hyperborea* | PAO | 260600 | 0.49 | 0.51 | 0.33 | 0.16 | 0.35 | 0.04 | 0.12 | 0.29 | 9 |
| 15 | Bacterial (treated with epimerase) | PAT | 438733 | 0.17 | 0.83 | 0 | 0.17 | 0.66 | 0 | 0.17 | 0 | 0 |
| 16 | Seaweed *Laminaria* | LFR5/60 | 34700 | 0.633 | 0.367 | 0.505 | 0.128 | 0.239 | 0.054 | 0.096 | 0.45 | 9.9 |
| 17 | Seaweed *Laminaria* | SF120 | 195000 | 0.664 | 0.336 | 0.545 | 0.119 | 0.218 | 0.061 | 0.083 | 0.484 | 9.6 |
| 18 | Seaweed *Laminaria* | SF/LF | 295000 | 0.66 | 0.336 | 0.548 | 0.116 | 0.22 | 0.042 | 0.081 | 0.506 | 13.8 |
| 19 | Seaweed *Laminaria* | SF200 | 387000 | 0.68 | 0.322 | 0.573 | 0.105 | 0.218 | 0.036 | 0.079 | 0.537 | 16.7 |
| 20 | Seaweed *Lessonia* | LF10L | 75000 | 0.45 | 0.553 | 0.275 | 0.19 | 0.362 | 0.068 | 0.153 | 0.19 | 4.4 |
| 21 | Seaweed *Lessonia* | LF120L | 221000 | 0.424 | 0.576 | 0.24 | 0.185 | 0.392 | 0.057 | 0.156 | 0.183 | 4.7 |
| 22 | Seaweed *Lessonia* | SF60 | 325000 | 0.411 | 0.589 | 0.219 | 0.195 | 0.393 | 0.077 | 0.155 | 0.139 | 3.3 |
| 23 | Seaweed *Lessonia* | H120L | 397000 | 0.45 | 0.551 | 0.276 | 0.173 | 0.379 | 0.051 | 0.15 | 0.22 | 5.9 |
| 24 | Seaweed *Laminaria* | XP3663 | 150000 | 0.60 | 0.40 | NA | NA | NA | NA | NA | NA | NA |

Figure 4:
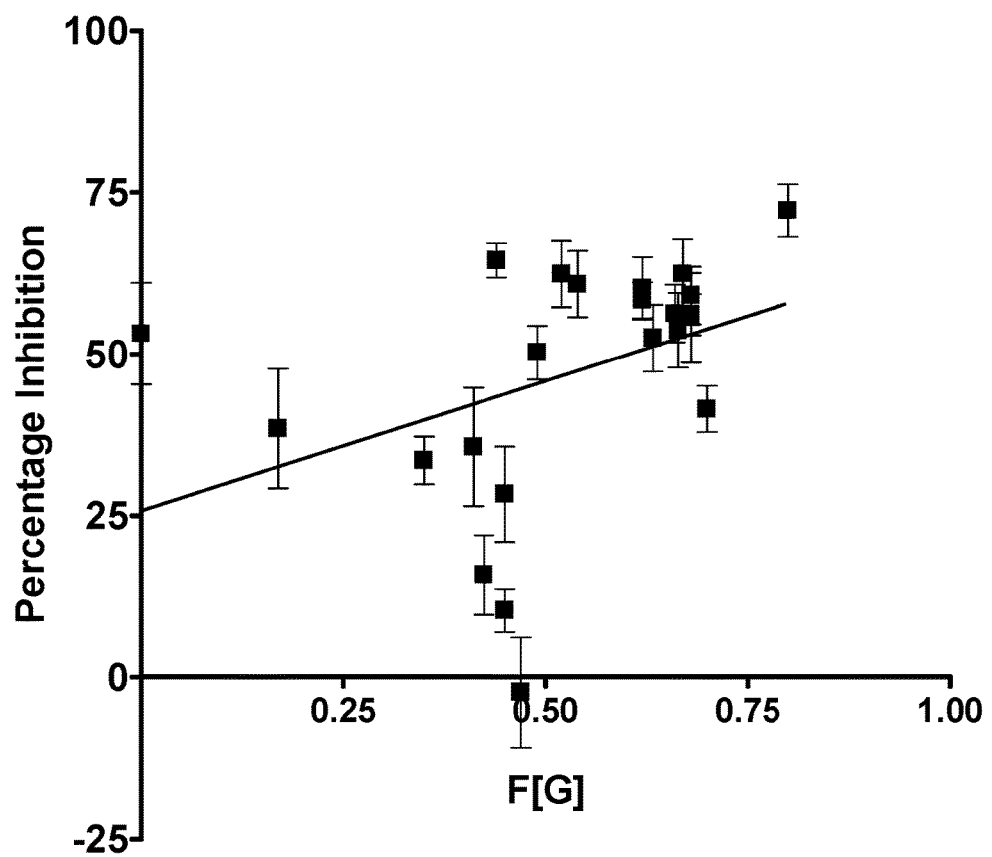
FIG. 4 is a graph showing the percentage of lipase inhibition at 12 minutes using 3.43 mg/ml alginate against the fraction of guluronate residues (F[G]) in the alginate polymer. Error bars show the standard error of the mean (n=6).
Figure 5:
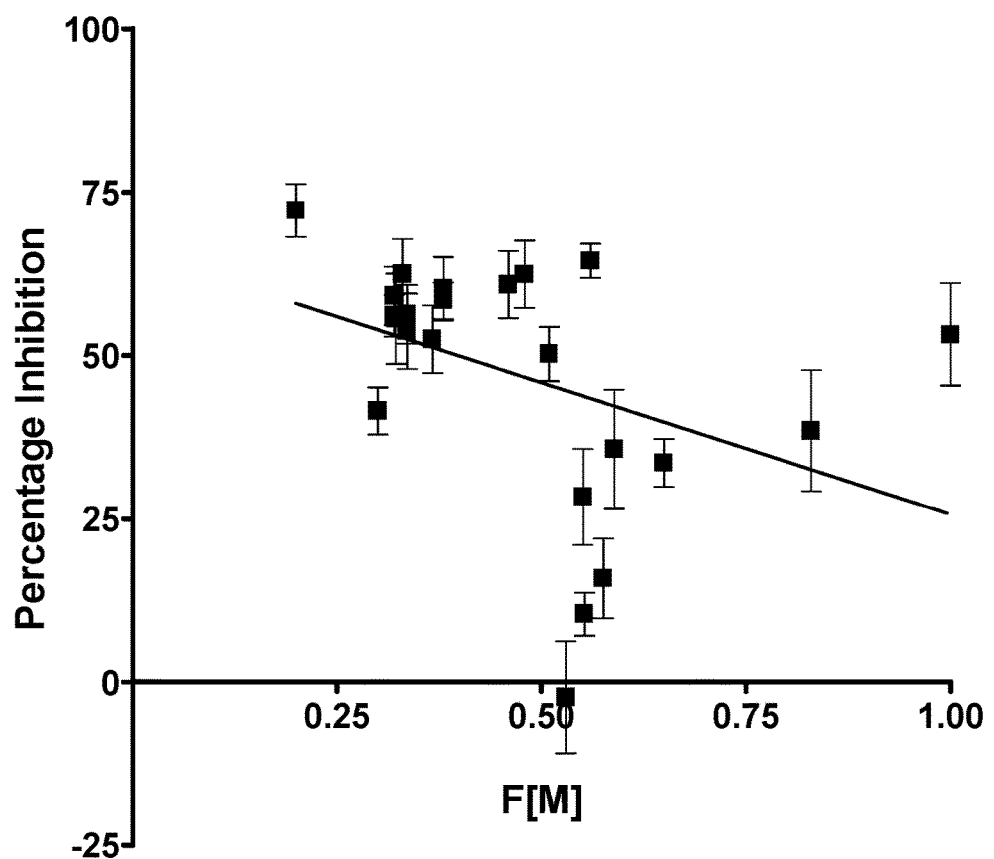
FIG. 5 is a graph showing the percentage of lipase inhibition at 12 minutes using 3.43 mg/ml alginate plotted against the fraction of mannuronate residues (F[M]) in the alginate polymers. Error bars shown are the standard error of the mean (n=6).

FIGS. 4 and 5 show that the fraction of mannuronic (M) or guluronic (G) acid residues (F(M) or F(G)) in an alginate had an impact on the ability of that alginate to reduce the level of pancreatic lipase activity. The Spearman rank correlation coefficient (r) in FIG. 4 is 0.502 showing that there is a positive relationship between the fraction of guluronate correlation calculation there is still a significant negative correlation with a Spearman value of −0.434 and a p value of 0.04.

Figure 10:
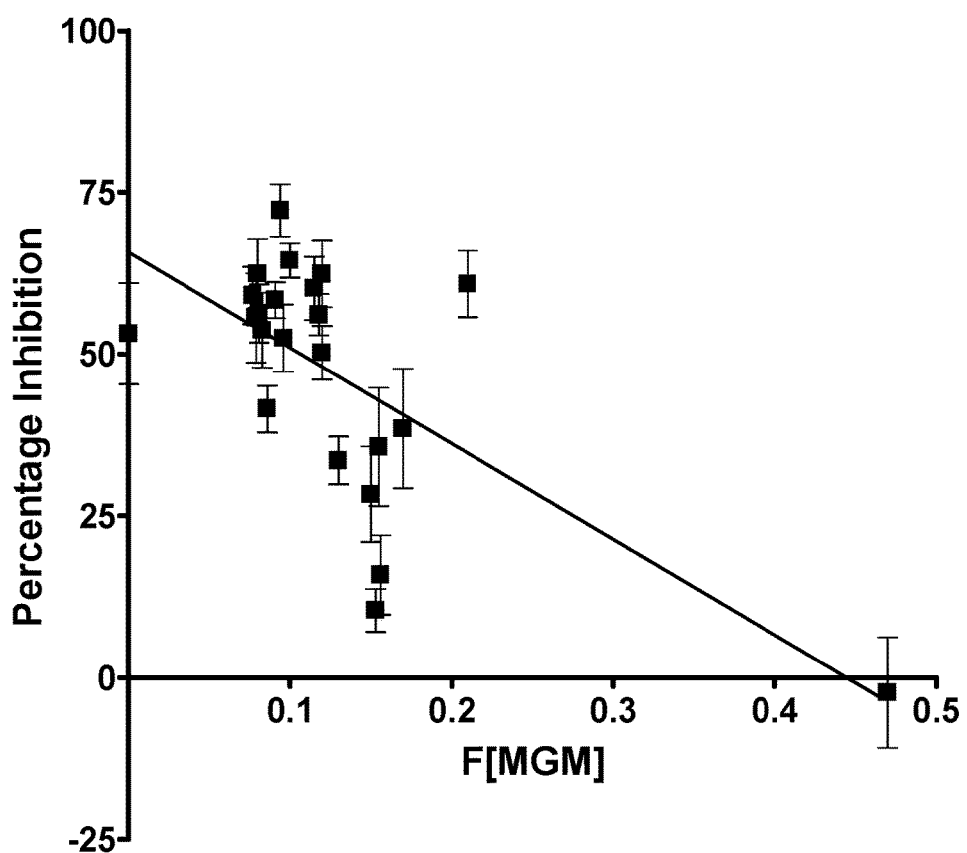
FIG. 10 is a graph showing the percentage of lipase inhibition at 12 minutes using 3.43 mg/ml alginate plotted against the fraction of MGM blocks (F[MGM]) in the alginate polymers. The error bars show the standard error of the mean (n=6).

Similarly, FIG. 10 shows that when the fraction of MGM blocks in the alginate polymer F(MGM) is compared to the percentage of lipase inhibition there is negative correlation.

The correlation of F(MGM) to lipase inhibition has a Spearman r value of −0.494 and a p value of 0.017. The correlation again may appear to be distorted by the extreme example of the poly-alternating bacterial alginate (F(MGM)=0.47). However in this case, when the result of the unique bacterial alginate is removed from the correlation calculation there is no significant correlation.

Figure 11:
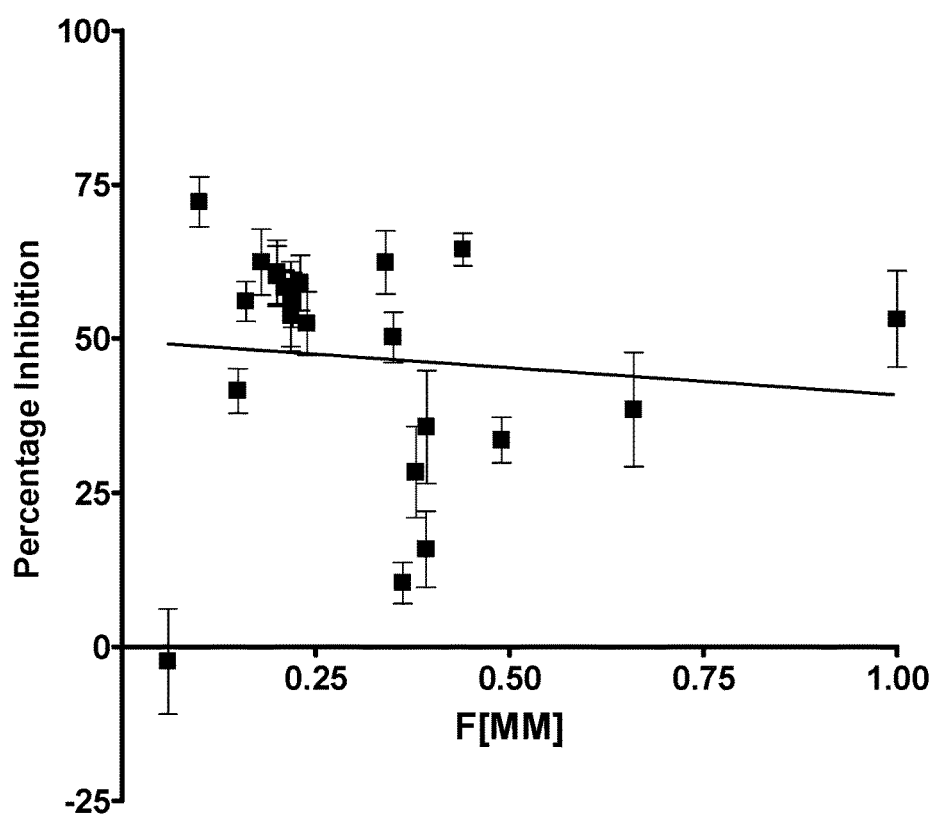
FIG. 11 is a graph showing the percentage of lipase inhibition at 12 minutes using 3.43 mg/ml alginate against the fraction of MM blocks F[MM] in the alginate polymers. The error bars show the standard error of the mean (n=6).
Figure 12:
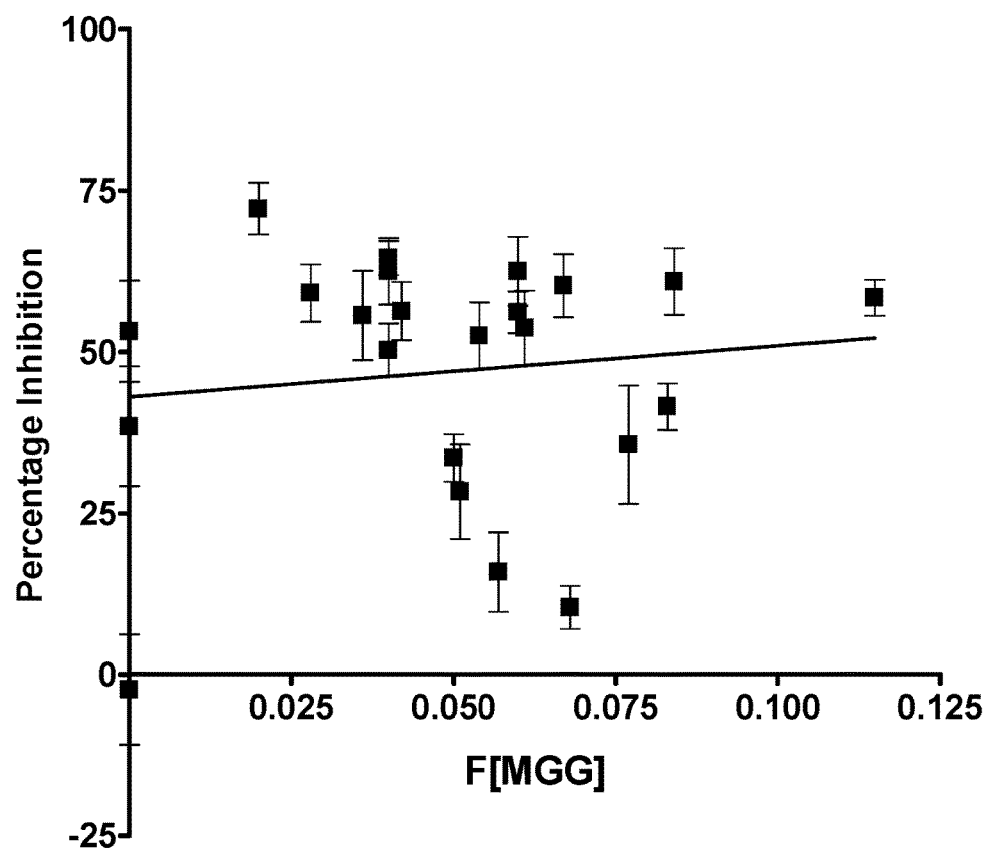
FIG. 12 is a graph showing the percentage of lipase inhibition at 12 minutes using 3.43 mg/ml alginate plotted against the fraction of either MGG or GGM blocks (F[MGG]) in the alginate polymers. The error bars show the standard error of the mean (n=6).

The fractions of MM blocks (FIG. 11) as well as MGG/GGM blocks (FIG. 12) in alginates were also compared against the level of lipase inhibition achieved. There was no statistically significant correlation between the values for either of the two block fractions. That is not to say, however, that there is no correlation in either of the figures, but that there are not enough data to suggest a significant correlation either positive or negative. In the two figures (FIGS. 11 and 12) the general tendency of the lines of best fit follows the trend of the data outlined above.

Figure 13:
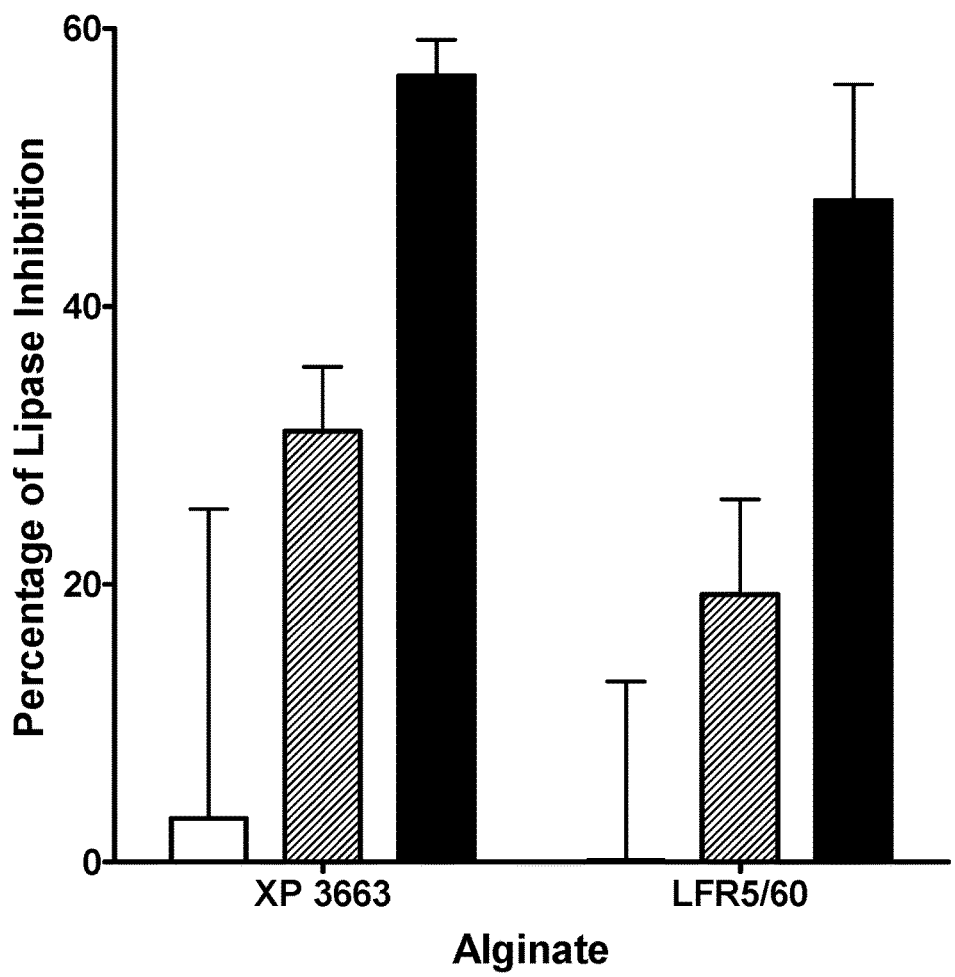
FIG. 13 is a bar chart showing the level of lipase inhibition achieved by alginates LFR5/60 and XP3663 at three concentrations: open bars—0.21 mg/ml, hatched bars—0.86 mg/ml and solid filled bars—3.43mg/ml. Error bars are the standard error of the mean (n=6).

FIG. 13 shows that alginate XP3663 was able to inhibit pancreatic lipase. The maximum level of lipase inhibition achieved by XP3663 was 56.6% (±6.4) at 3.43 g/l compared to LFR5/60 at the same concentration which achieved 47.6% (±11.4). At 0.86 g/l of alginate XP3663 achieved 31.0% (±6.4) whereas 'LFR5/60 achieved 19.3% (±16.7) and at 0.21 g/l of alginate XP3663 and 'LFR5/60 achieved 3.1% (±54.6) and 0.1% (±31.5) respectively. There is no significant difference between the two alginates at the same concentration using a two way ANOVA test.

REFERENCES

1. Penman, A. and G. Sanderson, *Method for Determination of Uronic Acid Sequence in Alginates*. Carbohydrate Research, 1972. 25(2): p. 273-282.
2. Smidsrod, O., *Molecular-Basis for Some Physical Properties of Alginates in Gel State*. Faraday Discussions, 1974. 57: p. 263-274.
3. Grasdalen, H., B. Larsen, and O. Smidsrod, *C-13-Nmr Studies of Alginate*. Carbohydrate Research, 1977. 56(2): p. C11-C15.
4. Smidsrod, O. and G. Skjak-Braek, *Alginate as immobilization matrix for cells*. Trends in Biotechnology, 1990. 8(3): p. 71-8.
5. Hoidal, H. K., et al., *The recombinant Azotobacter vinelandii mannuronan C-5-epimerase AlgE4 epimerizes alginate by a nonrandom attack mechanism*. Journal of Biological Chemistry, 1999. 274(18): p. 12316-12322.
6. Gimmestad, M., et al., *The Pseudomonas fluorescens AlgG protein, but not its mannuronan C-5-epimerase activity, is needed for alginate polymer formation*. Journal of Bacteriology, 2003. 185(12): p. 3515-3523.
7. Cygler, M.a.S., J. D., *Lipases and alpha/beta Hydrolase Fold*, in Methods in Enzymology, B.a.D. Rubin, E. A., Editor. 1997, Academic Press. p. 85/106.
8. Winkler, F. K., A. D'Arcy, and W. Hunziker, *Structure of human pancreatic lipase*. Nature, 1990. 343(6260): p. 771-774.
9. Egloff, M. P., et al., *The 2.46-Angstrom Resolution Structure of the Pancreatic Lipase-Colipase Complex Inhibited by a C-11 Alkyl Phosphonate*. Biochemistry, 1995. 34(9): p. 2751-2762.
10. Cambillau, C., Bourne, Y., Egloff, Martinez, C., and van Tilbeurgh, H., *Pancreatic Lipases and Their Complexes with Colipase and Inhibitors: Crystallization and Crysral Packing*, in Methods in Enzymology, B.a.D. Rubin, E. A., Editor. 1997, Academic Press. p. 107-118.
11. Hadvary, P., H. Lengsfeld, and H. Wolfer, *Inhibition of Pancreatic Lipase In vitro by the Covalent Inhibitor Tetrahydrolipstatin*. Biochemical Journal, 1988. 256(2): p. 357-361.
12. Drew, B. S., A. F. Dixon, and J. B. Dixon, *Obesity management: update on orlistat*. Vasc Health Risk Manag, 2007. 3(6): p. 817-21.
13. Panteghini, M., R. Bonora, and F. Pagani, *Measurement of pancreatic lipase activity in serum by a kinetic colorimetric assay using a new chromogenic substrate*. Annals of Clinical Biochemistry, 2001. 38: p. 365-370.

The invention claimed is:

1. A method of inhibiting pancreatic lipase, comprising the steps of:
   administering an effective amount of an alginate to a subject in need thereof; and
   inhibiting pancreatic lipase with the administered alginate;
   wherein the fraction of MGM blocks in the alginate is less than or equal to 0.21.
2. The method of claim 1, wherein the alginate is derived from seaweed.
3. The method of claim 1, wherein the alginate is a synthetic alginate.
4. The method of claim 1, wherein the alginate is a bacterial alginate.
5. The method of claim 1, wherein the fraction of the guluronate residues in the alginate is at least 0.5.
6. The method of claim 1, wherein the fraction of guluronate dimers in the alginate is at least 0.3.
7. The method of claim 1, wherein the fraction of guluronate trimers in the alginate is at least 0.25.
8. The method of claim 1, wherein the fraction of MGM blocks in the alginate is less than 0.2.
9. The method of claim 1, wherein use is directed to control of weight in animals, including human beings.
10. A method of inhibiting pancreatic lipase in an animal, including a human being, comprising the steps of:
    administering an effective amount of an alginate to an animal in need thereof; and
    treating a disease in the animal that is associated with increased levels of pancreatic lipase,
    wherein the fraction of MGM blocks in the alginate is less than or equal to 0.21.
11. The method of claim 10, wherein the amount of alginate administered is from 0.1 to 10 g as a daily dosage.

* * * * *